United States Patent [19]

Sandman

[11] Patent Number: 4,597,914

[45] Date of Patent: Jul. 1, 1986

[54] METHOD FOR THE PREPARATION OF AROMATIC SELENIUM COMPOUNDS

[75] Inventor: Daniel J. Sandman, Acton, Mass.

[73] Assignee: GTE Laboratories Incorporated, Waltham, Mass.

[21] Appl. No.: 507,156

[22] Filed: Jun. 23, 1983

[51] Int. Cl.[4] .................. C07C 163/00; C01B 19/04; C08G 79/00

[52] U.S. Cl. .................. 260/550; 528/397; 423/509

[58] Field of Search .............. 260/550; 528/397; 423/509

[56] References Cited

U.S. PATENT DOCUMENTS

| | | | |
|---|---|---|---|
| 3,149,101 | 9/1964 | Hubel et al. | 260/239 R |
| 3,354,129 | 11/1967 | Edmonds et al. | 528/265 |
| 3,671,467 | 6/1972 | Gunther | 528/397 X |
| 3,905,958 | 9/1975 | Gunther | 528/397 X |
| 3,965,049 | 6/1976 | Grushkin et al. | 520/1 |
| 4,286,018 | 8/1981 | Asakura et al. | 528/397 X |
| 4,344,869 | 8/1982 | Blinne et al. | 252/517 |

OTHER PUBLICATIONS

Balodis et al., *J. Org. Chem. USSR* (Engl. Transl.) 15, 343 (1979).
Gladysz et al., *J. Org. Chem.* 43, 1204 (1978).
Battistoni, P. et al., *Gazz., Chim. Ital. III*, 505 (1981).
Sandman, D. J. et al. (1982), *J. Chem. Soc., Chem. Commun.*, pp. 1133–1134.
Ohnishi, S. et al. (1982), *Chemistry Letters*, pp. 1841–1842.
Endres, H. et al. (1982), *Mol. Cryst. Liq. Cryst.* 86, 111–122.
K. Y. Jen et al., *J. Polymer Sci., Polymer Lett.* 21, 441 (1983).
S. Tanaka et al., *Makromol. Chem., Rapid Commun.* 4, 231–235 (1983).
T. Hasegawa et al., *J. Polymer Sci., Polymer Lett.* 22, 365 (1984).
Sandmann et al, *Organometalics*, vol. 2 (1983), pp. 549–551.
Okamoto et al., *Ann. N.Y. Acad. Sci.*, 192:60 (1972).

*Primary Examiner*—Donald G. Daus
*Assistant Examiner*—William A. Teoli, Jr.
*Attorney, Agent, or Firm*—Hamilton, Brook, Smith & Reynolds

[57] ABSTRACT

This invention constitutes a method for preparing molecular and polymeric aromatic selenide compounds such as bis-phenyl selenide and poly(p-phenylene selenide). The method comprises reacting an aryl halide with an alkali metal selenide reagent formed in an aprotic solvent.

11 Claims, No Drawings

METHOD FOR THE PREPARATION OF AROMATIC SELENIUM COMPOUNDS

DESCRIPTION

1. Field of the Invention

This invention is in the field of organic chemistry and relates to methods of synthesizing organometallic compounds containing selenium. Specifically, it relates to a method of synthesizing molecular and polymeric aromatic selenium compounds and a reagent useful in the preparation of such compounds.

2. Background of the Invention

Poly(p-phenylene sulfide) (PPS) is a crystalline, aromatic polymer comprising benzene rings linked with sulfur atoms in the para position. The polymer exhibits several advantageous properties including high-temperature stability, flame resistance and good chemical resistance. PPS is used widely as a coating material and in injection and compression molding processes. Recently PPS has received attention as an example of a polymer without a continuous carbon $\pi$ system which becomes highly conducting on exposure to strong oxidants. See e.g., European Patent Application No. 80107176.2.

The usefulness of PPS has generated interest in the selenium analog of PPS, poly(p-phenylene selenide) (PPSe). At least one unsuccessful attempt to prepare PPSe from $Na_2Se$ and p-dibromobenzene in ethyl acetate solution has been reported. See, Okamoto et al., *Ann. N.Y. Acad. Sci* 192:60 (1972). Balotis et al. have reported the synthesis of the metallocyclic compound tetraselenotetracene from sodium diselenide ($Na_2Se_2$) in dimethylformamide solution.

SUMMARY OF THE INVENTION

This invention constitutes a method for the synthesis of conjugated molecular and polymeric aromatic selenium compounds. The method involves the reaction of aromatic halides with an alkali metal monoselenide reagent such as $Na_2Se$ or $K_2Se$. According to the method of this invention, the alkali metal selenide reagent is formed directly from an alkali metal and selenium in a polar aprotic solvent, and the reagent is then reacted with an appropriate aromatic halide in the same solvent system to form the desired molecular or polymeric organic selenium compound.

Examples of some of the molecular aromatic selenides which may be synthesized by this method are bis-phenyl selenide, bis(2-naphthyl) selenide and bis(9-anthracenyl) selenide. Molecular aromatic selenides have useful bactericidal activity, antiseptic activity and anti-inflammatory activity. See e.g. "Organic Selenium Compounds: Their Chemistry and Biology" ed. D. L. Klayman and W. H. H. Gunther, Wiley-Interscience (1973). Examples of some of the polymeric aromatic selenides which may be produced are poly(p-phenylene selenide) and poly(9,10-anthraceneselenide). Polymeric aromatic selenides are precursors to conducting polymers.

The invention provides a simple and direct method for synthesizing previously-known and new organoselenium compounds. The method eliminates the use of liquid ammonia or other nitrogenous solvents, which are used currently in the synthesis of organoselenium compounds, and thus provides for the synthesis of these compounds under significantly milder conditions.

BEST MODE OF CARRYING OUT THE INVENTION

The alkali metal selenide reagent is formed in an aprotic solvent such as N,N-dimethylformamide, hexamethylphosphoramide or N-methylpyrrolidinone. Finely divided elemental selenium is added to the solvent, and a suspension of selenium is formed by stirring. The suspension is heated to about 100° C. and then pieces of alkali metal are added to form a mixture in which the molar ratio of alkali metal to selenium is about 2:1. The resulting alkali metal selenide has the chemical formula $M_2Se$ wherein M is an alkali metal.

The alkali metal employed in the production of the intermediate selenide reagent may be lithium, sodium or potassium. Sodium however is the preferred metal because it is most convenient to use.

The reaction to form the alkali selenide reagent, and the reaction of the alkali selenide reagent with the aromatic halogen compound may be carried out in the same solvent. Thus, after the reagent is synthesized, the aromatic halogen reactant is added directly to the reaction mixture containing the alkali selenide reagent. The entire synthetic procedure may be carried out under an atmosphere of an inert gas such as argon or one of the other noble gases. This prevents undesirable side reactions with moisture or the components of air.

After the intermediate alkalide selenide reagent is reacted with an aromatic halogen compound to form the desired molecular or polymeric organic selenide, the product is then separated from the reaction mixture by conventional techniques. For the most part the resulting selenide compounds are not air-sensitive and therefore may be subjected to purification techniques such as recrystallization, sublimation or the like without exercise of excessive care.

According to the method of this invention, bis aryl selenide compounds are produced by the alkali metal selenide reagent with a monohaloaromatic compound. The reaction between the alkali metal selenide and the aryl halide in a molar ratio of substantially 1:2 gives products of the general formula Ar-Se-Ar where Ar signifies the particular aromatic group of the aryl halide reactant. The synthesis of bis aryl selenides is typified by the reaction of 2-bromonaphthalene with sodium selenide to give bis-($\beta$-naphthyl)selenide.

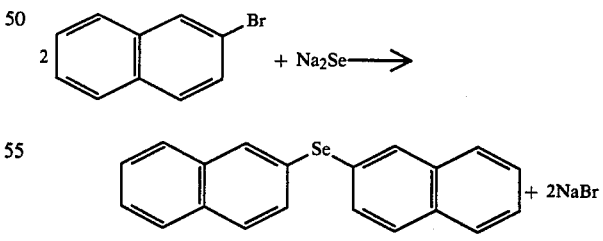

Aromatic polymers are produced by reacting the alkali metal selenide reagent with a dihalo-aromatic compound. The reaction between the alkali metal selenide and the dihalo-aromatic compound in a molar ratio of substantially 1:1 gives polymeric aromatic selenides of the general formula

The synthesis of organic polymeric selenides is typified by the reaction of p-dibromobenzene with sodium selenide to give poly-(p-phenylene selenide) (PPSe).

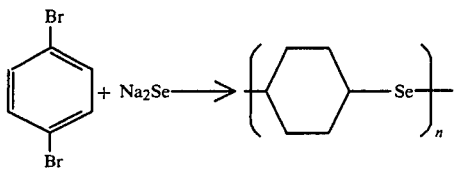

As shown in the equation, p-dibromobenzene reacts with the sodium selenide reagent to form PPSe. Notably, these reaction conditions are significantly milder than those used for the synthesis of poly(p-phenylene sulfide) (PPS). It is suspected that the facility of the reaction is due to the operation of an $S_{RN}1$ mechanism.

The polymeric selenides, such as PPSe and poly(9,10-anthraceneselenide), are useful as precursors to conducting polymers. For example, exposure to PPSe to arsenic pentafluoride (at 100 Torr) for 5 hours at 40° C. results in a conductivity for the treated polymer of about $10^{-2}$–$10^{-3}$ (ohm cm)$^{-1}$.

The following specific examples further illustrate the invention.

EXAMPLE 1

Preparation of poly(p-phenyleneselenide)

To a magnetically stirred suspension of selenium (2.17 g, 0.0275 gm-atom) in N-methylpyrrolidinone (50 ml) under argon at ca. 110° was added pieces of sodium (1.30 g, 0.055 gm atom) over a one hour period. After stirring for an additional thirty minutes, solid p-dibromobenzene (5.90 g, 0.025 mole) was added, and the mixture was heated at 170° for twenty hours. The mixture was allowed to cool to room temperature and solid product was precipitated with methanol and water. The product was filtered and washed consecutively with saturated sodium sulfide, water, and methanol. The yellowish solid was Soxhlet extracted for 15 hours with tetrahydrofuran to give a yellow solid, 0.395 g (10% yield). The x-ray diffraction pattern of this solid exhibits a strong reflection at $2\theta = 20.0°$ (d=4.44 Å) compared to PPS(3) which exhibits a strong reflection at d=4.36 Å. An elemental analysis of the product yielded the following results:

Calculated for —$C_6H_4Se$—$_x$: C, 46.48; H, 2.60; Se=50.92. Found: C, 43.23; H, 2.54; Se, 50.06.

EXAMPLE 2

Preparation of poly-p(phenyleneselenide) from p-dibromobenzene in N,N-dimethylformamide A sodium selenide reagent was prepared in N,N-dimethylformamide (40 ml) from sodium (1.30 g, 0.055 gm atom) and selenium (2.17 g 0.0275 gm atom) at 100°-110° C. under argon. To this mixture, p-dibromobenzene (5.90 g, 25 mmole) was added, and the mixture was heated for twenty hours. The reaction mixture was diluted with methanol (40 ml) and poured into saturated sodium chloride. The solid precipitate was filtered and washed sequentially with water (100 ml), warm sodium sulfide solution (200 ml), water (100 ml), and methanol (60 ml). The solid was continuously extracted with tetrahydrofuran until the extracts were colorless. The remaining solid after vacuum drying weighed 3.10 g (80% yield) and on heating in a capillary darkened at 200° and melted irreversibly by 233°. An elemental analysis for the product yielded the following results:

Calculated for —$C_6H_4Se$—$_n$: C, 46.48; H, 2.60; Se, 50.92. Observed: C, 41.36; H, 2.26; Se, 52.15; Br, 1.57.

The observed elemental analysis corresponds to a composition of $C_{6.0}H_{3.91}Se_{1.15}$ and based on bromine analysis, a molecular weight of 5000 or 10,000 is estimated for one and two bromine atoms per polymer chain, respectively. The 15% atomic excess of selenium is attributed to diselenide linkages in the polymer. The x-ray diffraction pattern of this polymer is similar to that described in Example 1 and shows no elemental selenium.

EXAMPLE 3

Preparation of PPSe from p-dichlorobenzene in N,N-dimethylformamide (DMF)

A sodium selenide reagent was prepared in DMF (40 ml) in the usual manner from selenium (2.17 g, 0.0275 gm-atom) and sodium (1.30 g, 0.055 gm-atom under argon. To this reagent was added p-dichlorobenzene (3.675 g, 25 mmole). This mixture was kept at a bath temperature of 140°-145° for 18 hours and then at 170°-175° for 100 hours. The product was isolated as previously described to give PPSe as a light brown powder, 0.188 g, 4.85% yield. The infrared spectrum and x-ray diffraction pattern corresponded to those of PPSe.

EXAMPLE 4

Preparation of PPSe from p-dichlorobenzene in N-methylpyrrolidinone (NMP)

A sodium selenide reagent was prepared in NMP (15 ml) from sodium (1.30 g) and selenium 2,17 g) under argon. To this reagent was added p-dichlorobenzene (3.675 g), and the mixture was heated at bath temperature 155°-160° for sixteen hours and then at 160°-170° for eighty hours. The product was isolated as previously to give PPSe, 0.553 g, 14.3% yield, with an infrared spectrum in accord with previous observations.

EXAMPLE 5

Preparation of PPSe from p-dibromobenzene and K$_2$Se

A potassium selenide reagent was prepared in DMF (40 ml) under argon from potassium (2.15 g, 0.055 gm—atom) and selenium (2.17 g, 0.0275 gm—atom). To this was added p-dibromobenzene (5.90 g, 25 mmole) and the mixture was heated at 145°-150° for 40 hours. The product was isolated in the usual manner to give PPSe (602 mg, 15.5% yield), m.p. 221°-245° with infrared spectrum and x-ray diffraction pattern in accord with earlier samples of PPSe.

EXAMPLE 6

Preparation of poly(9,10-anthraceneselenide)

To a magnetically stirred suspension of selenium (0.79 g, 0.01 gm atom) in N,N-dimethylformamide (DMF, 20 ml) under argon at ca. 120° C. was added pieces of sodium (0.46 g, 0.02 gm atom), followed by an additional 60 ml DMF. 9,10-Dibromoanthracene (3.36 g, 0.01 mole) was added as a solid, and the mixture was heated at 120°-130° for twenty hours. The cooled mixture was filtered to give a yellow-orange solid which was consecutively washed with saturated sodium sulfide, water, and methanol, followed by vacuum drying to give 0.98 g powder (38% yield), mp 300°. The product was amorphous by x-ray diffraction, and its solid state spectrum, measured by diffuse reflectance, exhibits a absorption maximum at 460 nm. An elemental analysis for the product yielded the following results:

Calculated for $(C_{14}H_8Se)_x$: C, 65.90; H, 3.16; Se, 30.94. Found: C, 63.12; H, 3.23; Se, 30.27; Br, 1.57.

EXAMPLE 7

Preparation of Bis(9-anthracenyl) selenide

To a magnetically stirred suspension of selenium (0.295 g, 0.00375 gm atom) in DMF (15 ml) at 110° C. was added sodium (0.173 g, 0.0075 gm atom). After one hour, 9-bromoanthracene (0.482 g, 1.88 mmole) followed by DMF (15 ml) was added. The mixture was heated at 140° for 16 hours when it was cooled to room temperature and poured into water. This mixture was extracted with dichloromethane; the extracts were dried over magnesium sulfate and evaporated. The residue was chromatographed on silica gel in hexane, and the desired product crystallized from a dichloromethanechloroform mixture to give 0.250 g (31% yield), mp 259°–263°, identified by the molecular ion in the mass spectrum.

EXAMPLE 8

Preparation of bis-($\beta$-Naphthyl) selenide from 2-bromonaphthalene and $K_2Se$.

A potassium selenide reagents was formed in hexamethylphosphoramide (40 ml) from potassium (0.78 gm, 0.02 gm—atom) and selenium (0.79 g, 0.01 gm—atom) under argon at 70°–80°. The bath temperature was raised to 90°–100° over thirty minutes and 2-bromonaphthalene (4.14 g, 0.02 mmole) was added. Bath temperature was raised to 170°–180° and after 23.5 hours at that temperature, the mixture was allowed to cool to room temperature and poured into salt water (150 ml). A dark precipitate was isolated by filtration and volatiles were removed by vacuum sublimation. The residue was chromatographed on silica gel (40 g) and eluted with 50:50 v/v hexane-benzene. One gram of white solid and the desired compound was isolated; the analytical sample exhibited m.p. 131°–133°. The following absorption spectrum was observed in hexane solution, $\lambda_{max,nm}$ ($\log_{10} \epsilon$): 335sh(3.63), 307sh (4.11), 299sh (4.16), 278sh (4.25), 259sh (4.59), 252sh (4.55), 229sh (5.05).

An elemental analysis of the product yielded the following results: Calculated for $C_{20}H_{14}Se$: C, 72.07; H, 4.23; Se, 23.69. Found: C, 72.06; H, 4.00; Se, 23.88.

What is claimed is:

1. A method of preparing monomeric and polymeric aromatic organic selenium compounds comprising reacting a suspension of finely divided selenium with an alkali metal in a polar aprotic solvent, wherein the molar ratio of alkali metal to selenium is about 2:1, to produce an alkali metal monoselenide reagent; and reacting said alkali metal monoselenide reagent with monohalo-aromatic compound to produce a bis-aryl selenide characterized by the formula Ar-Se-Ar, wherein Ar signifies the aryl group, or with a dihalo-aromatic compound to produce a polymeric aromatic selenium compound characterized by the formula $(Ar—Se)_n$ wherein Ar is an aryl group and n is an integer greater than 1, the polymeric aromatic selenium compound having a selenium content of not more than about 15% in excess of a stoichiometric amount.

2. A method of claim 1 wherein the alkali metal is sodium or potassium.

3. A method of claim 2 wherein the polar aprotic solvent is N-methylpyrrolidinone, N,N-dimethylformamide or hexamethylphosphoramide.

4. A method of claim 1 wherein the halogen substituent of said monohalo-aromatic compound is chlorine, bromine or iodine.

5. A method of claim 1 wherein the halogen substituent of said dihalo-aromatic compound is chlorine, bromine or iodine.

6. A method of claim 1 wherein the dihalo-aromatic compound is selected from the group comprising p-dibromobenzene, p-dichlorobenzene or p-diodobenzene whereby poly(p-phenylene selenide) is produced.

7. A method of preparing an alkali metal selenide reagent useful for synthesizing organic compounds containing selenium consisting of reacting a suspension of finely divided selenium with an alkali metal in a polar aprotic solvent, wherein the molar ratio of alkali metal to selenium is about 2:1, to produce said alkali metal monoselenide reagent.

8. A method of claim 7 wherein the alkali metal is sodium or potassium.

9. A method of claim 7 wherein the polar aprotic solvent is N-methyl pyrrolidinone, N,N-dimethylformamide or hexamethylphosphoramide.

10. A method of preparing a poly(p-phenylene selenide) having a selenium content of not more than about 15% in excess of stoichiometric amount, comprising the steps of:

a. reacting a suspension of finely divided selenium with an alkali metal in a polar aprotic solvent, the molar ratio of alkali metal to selenium being about 2:1, to produce an alkali metal monoselenide reagent; and b. reacting the alkali metal monoselenide reagent with a para-dihalogenated benzene in the solvent to produce poly(p-phenylene selenide) characterized by the general formula $(C_6H_4Se)_n$, wherein n is an integer greater than 1, the poly(p-phenylene selenide) having a selenium content of about 15% or less in excess of a stoichiometric amount.

11. A method of claim 10, wherein the alkali metal is sodium, potassium or lithium and the polar aprotic solvent is N-methylpyrrolidinone, N,N-dimethylformamide or hexamethylphosphoramide.

* * * * *